(12) United States Patent
Weinberg

(10) Patent No.: US 11,534,771 B2
(45) Date of Patent: Dec. 27, 2022

(54) METHOD AND APPARATUS FOR MEASURING AND INACTIVATING PATHOGENS USING MAGNETIZABLE DEVICES IN A BODY

(71) Applicant: WEINBERG MEDICAL PHYSICS INC., North Bethesda, MD (US)

(72) Inventor: Irving Weinberg, North Bethesda, MD (US)

(73) Assignee: WEINBERG MEDICAL PHYSICS INC, North Bethesda, MD (US)

( * ) Notice: Subject to any disclaimer, the term of this patent is extended or adjusted under 35 U.S.C. 154(b) by 0 days.

(21) Appl. No.: 16/900,414

(22) Filed: Jun. 12, 2020

(65) Prior Publication Data

US 2021/0363513 A1 Nov. 25, 2021

Related U.S. Application Data

(60) Provisional application No. 63/029,518, filed on May 24, 2020.

(51) Int. Cl.
*B03C 1/28* (2006.01)

(52) U.S. Cl.
CPC .......... *B03C 1/28* (2013.01); *B03C 2201/22* (2013.01); *B03C 2201/26* (2013.01)

(58) Field of Classification Search
USPC ........................................... 607/103
See application file for complete search history.

(56) References Cited

U.S. PATENT DOCUMENTS

| | | | | |
|---|---|---|---|---|
| 2002/0133115 A1* | 9/2002 | Gordon | ................... | A61L 29/16 604/96.01 |
| 2007/0255086 A1* | 11/2007 | Nehls | ..................... | A61N 1/056 600/12 |
| 2010/0204674 A1* | 8/2010 | Forbes | .................. | A61L 31/022 604/500 |
| 2010/0303716 A1* | 12/2010 | Jin | ..................... | A61M 37/0092 424/1.11 |
| 2013/0261373 A1* | 10/2013 | Pison | ..................... | A61N 2/004 600/12 |
| 2013/0267762 A1* | 10/2013 | Levy | .................... | A61K 9/5115 600/12 |
| 2017/0143233 A1* | 5/2017 | Audeh | ............... | A61K 49/0058 |

\* cited by examiner

*Primary Examiner* — David C Mellon
(74) *Attorney, Agent, or Firm* — Barnes & Thornburg LLP

(57) ABSTRACT

An apparatus and method collect and deactivate pathogens (for example, coronaviruses) within a magnetic particle in order to reduce the number of active pathogens in a body.

19 Claims, 5 Drawing Sheets

METHOD AND APPARATUS FOR MEASURING AND INACTIVATING PATHOGENS USING MAGNETIZABLE DEVICES IN A BODY

CROSS REFERENCE AND PRIORITY CLAIM

This patent application claims priority to U.S. Provisional Patent Application Ser. No. 63/029,518, entitled "METHOD AND APPARATUS FOR MEASURING AND INACTIVATING PATHOGENS USING MAGNETIZABLE DEVICES IN A BODY," filed May 24, 2020, the disclosure of which being incorporated herein by reference in its entirety.

FIELD

Disclosed embodiments pertain to methodologies and equipment for pathogen inactivation within a body using magnetizable materials.

BACKGROUND

It is known that timely administration of materials that bind noxious chemicals can reduce the extent of disease by reducing the concentration of these noxious chemicals in the body. For example, activated charcoal is often recommended after ingestion of poisons, and ethylenediamine tetraacetate (EDTA) is recommended after lead poisoning.

Some pathogens can be bound to certain chemical compounds (considered "receptors"). For example, the publication entitled "Structural basis for human coronavirus attachment to sialic acid receptors" by M. A. Tortorici et al in the 2019 journal Nature Structural & Molecular Biology taught that coronavirus would bind to 9-0-acetylated sialic acids.

Some pathogens (for example, amoebas) can be attracted to chemical compounds, as taught by S. Blazquez et al in the journal Infection and Immunity 2006 article entitled "Human Tumor Necrosis Factor is a Chemoattractant for the Parasite *Entamoeba histolytica.*"

Additionally, it is known that some cancer cells can be attracted to chemical compounds, as taught by C. E. Green et al in the journal PLOS Biology 2009 article entitled "Chemoattractant Signaling between Tumor Cells and Macrophages Regulates Cancer Cell Migration, Metastasis and Neovascularization".

Further, it is known that magnetic particles can be administered to a person, and that the magnetic particles may contain and release drugs or other compounds. It is known that the magnetic properties of such particles may be used to advantage by applying magnetic fields to the body so that the particles preferentially accumulate in certain locations.

A magnetic instrument may be used to detect the change of state in a magnetic nanoparticle when the nanoparticle is bound to a chemical, as taught by A. Tomitaka et al in the Nanoscale 2019 article entitled "Dynamic magnetic characterization and magnetic particle imaging enhancement of magnetic-gold core-shell nanoparticles".

Further, a magnetic instrument can be used to detect the distance between sections of a magnetic particle, as taught by G. Zabow, S. J. Dodd and A. P. Koretsky in the Nature 2008 letter entitled "Shape-changing magnetic assemblies as high-sensitivity NMR-readable nanoprobes."

SUMMARY

Disclosed embodiments provide an apparatus and method for collecting and deactivating pathogens (for example, coronaviruses) within a magnetic particle in order to reduce the number of active pathogens in a body.

DETAILED DESCRIPTION

Disclosed embodiments provide an apparatus and method for collecting and deactivating pathogens (for example, coronaviruses) within a magnetic particle in order to reduce the number of active pathogens in a body.

For the purposes of this disclosure, the term "pathogen" is meant to include microbes (for example, viruses, bacteria or fungi) that cause disease as well as substances that cause disease (for example, poisons, cytokines, renal calcifications, arterial plaque) or cells that cause disease (for example, cancer cells or sickle cells). For clarity, the terms "particle" and "device" may be used interchangeably to mean a component administered to a body, since "magnetic particle" is a term used by the public to mean a device or particle containing magnetizable materials. The term "particle" does not mean the device need be small. Rather, the device may be 10 nanometers in width and 200 nanometers in length (as might be appropriate to deal with viruses) or may be up to millimeters in width and millimeters in length (as might be appropriate to deal with parasites). The term "fillable section" of a device is intended to mean a space bounded at least in part by components of a device, wherein that space can be filled with fluid and/or pathogens.

Figure 1:
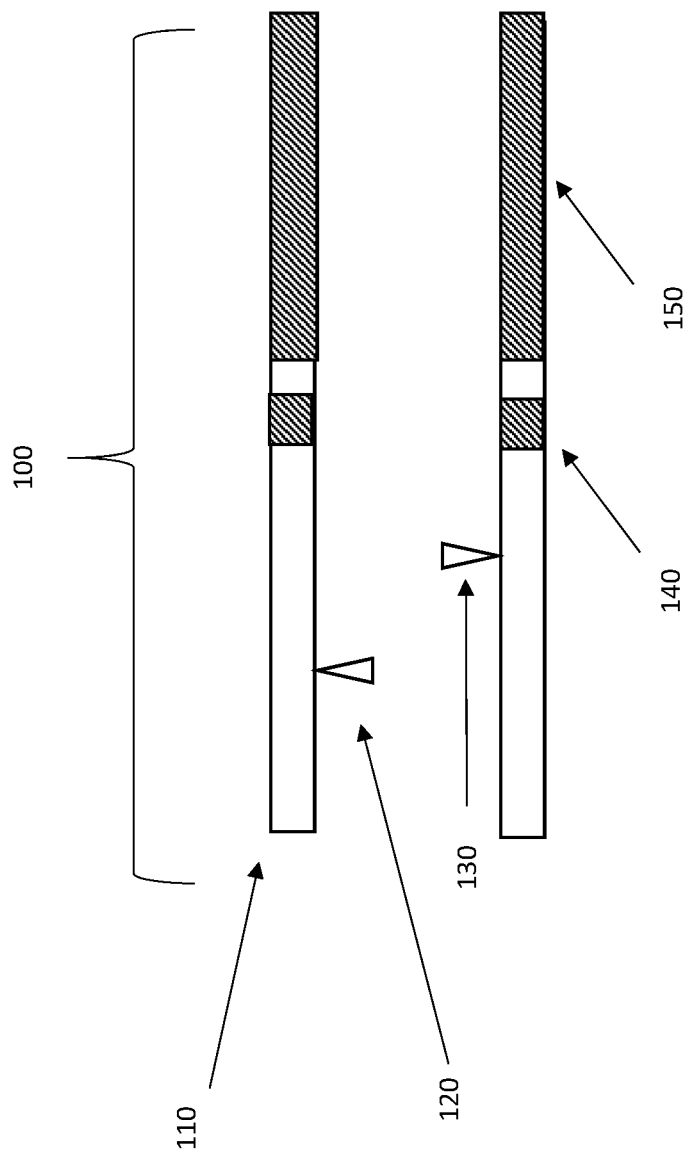
FIG. 1 shows an example of one embodiment of the disclosed embodiments.

FIG. 1 shows an example of one embodiment of the disclosed embodiments. The apparatus consists of a system including at least one device 100 containing a fillable section. Device 100 may be hollow throughout as shown in FIG. 1 or may be only partially hollow. Device 100 has a wall section 110 which may be gold or iron or other materials. In FIG. 1, the device appears to be cylindrical however it may be another shape with a hollow section. Device 100 contains a material 120 that binds to a pathogen so that the pathogen temporarily or permanently remains within the device. A structure (for example a polymer) eluting a chemoattractant or other chemical substance for attracting a pathogen may be included within the device (as in 130) or outside the device. Device 100 includes at least one magnetizable section 150 upon which a torque or force may be applied by a magnetic field. Device 100 may include one or more additional magnetizable section 140 upon which a torque or force may be applied by a magnetic field.

Figure 2:
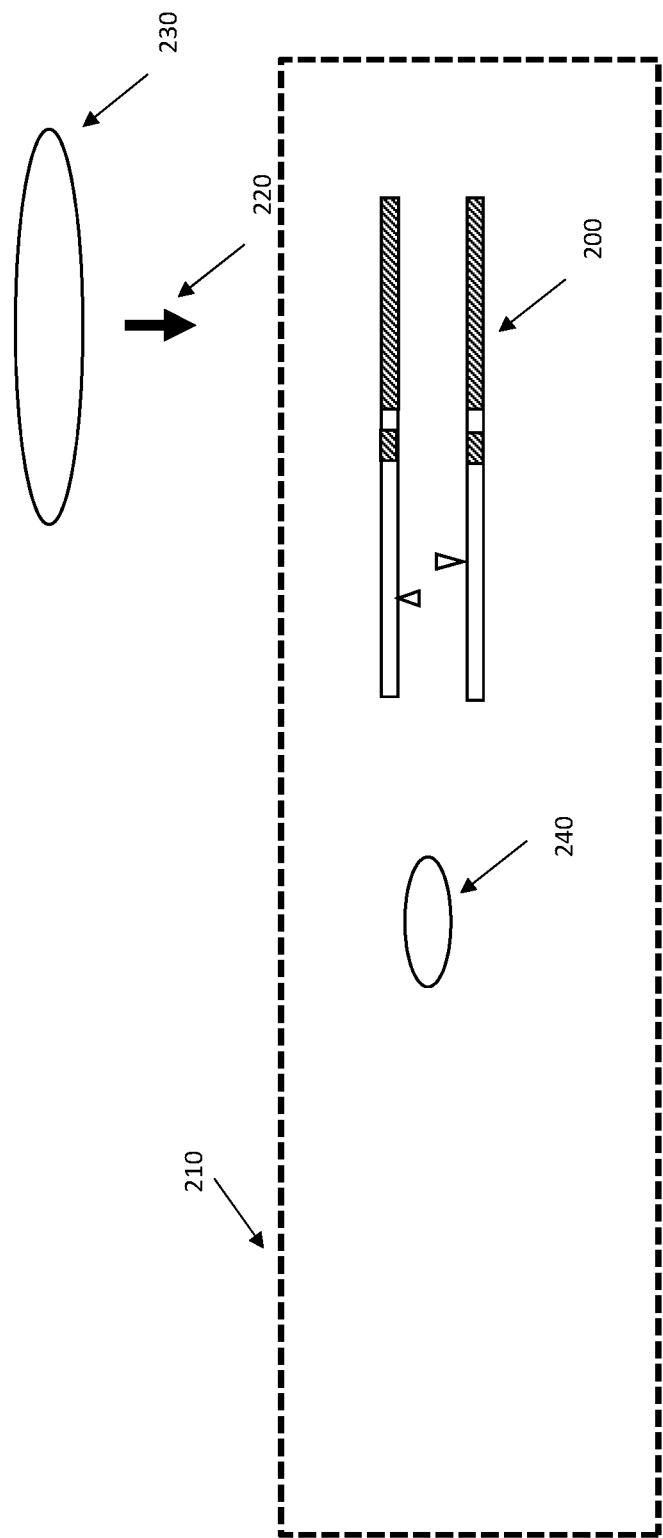
FIG. 2 provides an illustration of how the device of FIG. 1 may be used in a body 210.

FIG. 2 shows how the device of FIG. 1 (now numbered 200) may be used in a body 210. A magnetic field 220 is generated by a coil or magnet or other electromagnetic actuator or antenna 230 that is outside the body. Electromagnetic actuator or antenna 230 may also be part of a system for imaging the body and/or device 100. Magnetic field 220, under the operation of a computer (not shown) may manipulate device 200 in body 210 to a desired location in body 210 by exerting a force on sections 140 or 150 of device 200. Magnetic field 220 may rotate device 200 by exerting a torque on section 140, in order to better penetrate or otherwise travel through tissues in the body. Pathogen 240 may be attracted to segment 130, and thereby be drawn into the fillable section of device 200. Pathogen 240 may be immobilized in device 200 through binding with segment 120. Device 200 may be heated to destroy or inactivate pathogen 240, for example with the application of external oscillating magnetic fields with coil or magnet 230 that heat section 150 or by application of electromagnetic radiofrequency radiation from an antenna (not shown) that can heat particle wall 110 (which may be electrically conductive).

Figure 3:
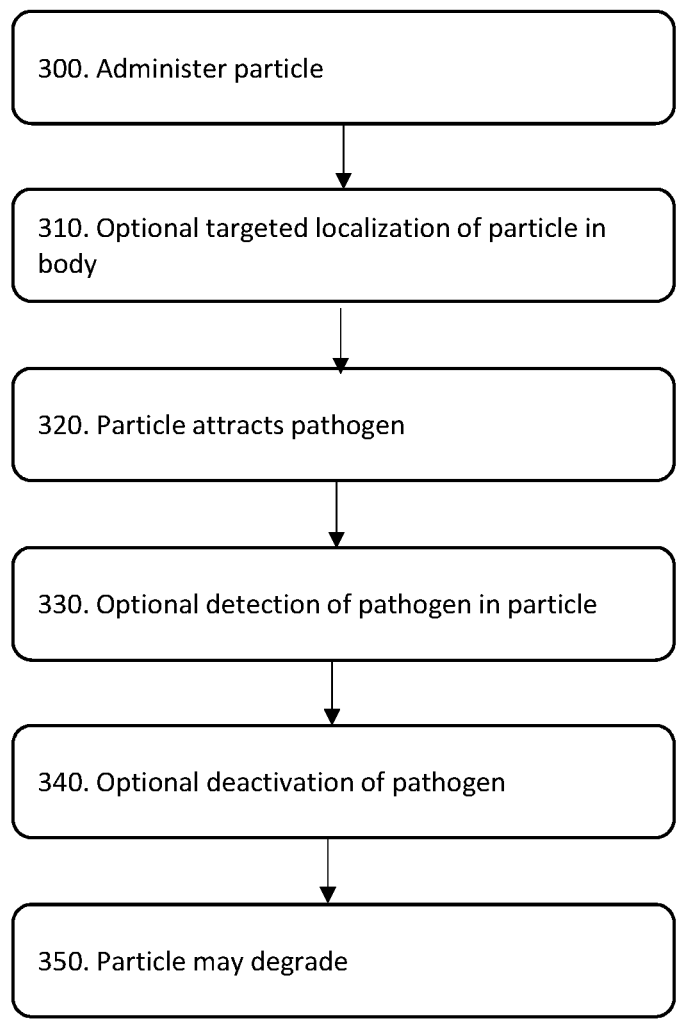
FIG. 3 illustrations operations of one example of the disclosed embodiments in the method.

The above method operations of one example of the disclosed embodiments are illustrated in the flow chart of FIG. 3. Although the term "subsequent operation" is used in the next section of this specification for illustration of the method of the disclosed embodiments, it is understood that some operations may be in different orders and may be repeated or omitted.

In operation 300, one or more particles (for example, device 200) are administered to a body (for example, orally or by inhalation or by intravenous injection). In subsequent operation 310, the particles are optionally guided to a location of interest in the body, for example by application of a magnetic field 220. Alternatively, the particles may accumulate particularly in a location of interest, for example, if the particles were decorated with an antibody or other means of binding to a specific tissue type or types. Or alternatively, the particles could do their work anywhere in the body, or in subsystems such as the circulation of the body.

Subsequent operation 320 is the attraction of the pathogen into the fillable section of the device.

Operation 330 is the optional detection of the pathogen, for example by altering the electromagnetic signal emitted by the particle in response to a changing magnetic field (as has been shown to be detectable with magnetic particle imaging).

In subsequent operation 340, the pathogen may be deactivated, for example by magnetically heating the particle or by rotating the particle to apply destructive shear forces on the pathogen or by pressing on the pathogen to crack it. Alternatively, the particle may incorporate magnetoelectric materials that may apply an electrical pulse to the pathogen.

In subsequent operation 350, the particle may optionally be eliminated from the body, for example through oxidation of the components of the particle or digestion by tissues in the body and subsequent excretion. Such components are referred to as being "biodegradable".

Figure 4:
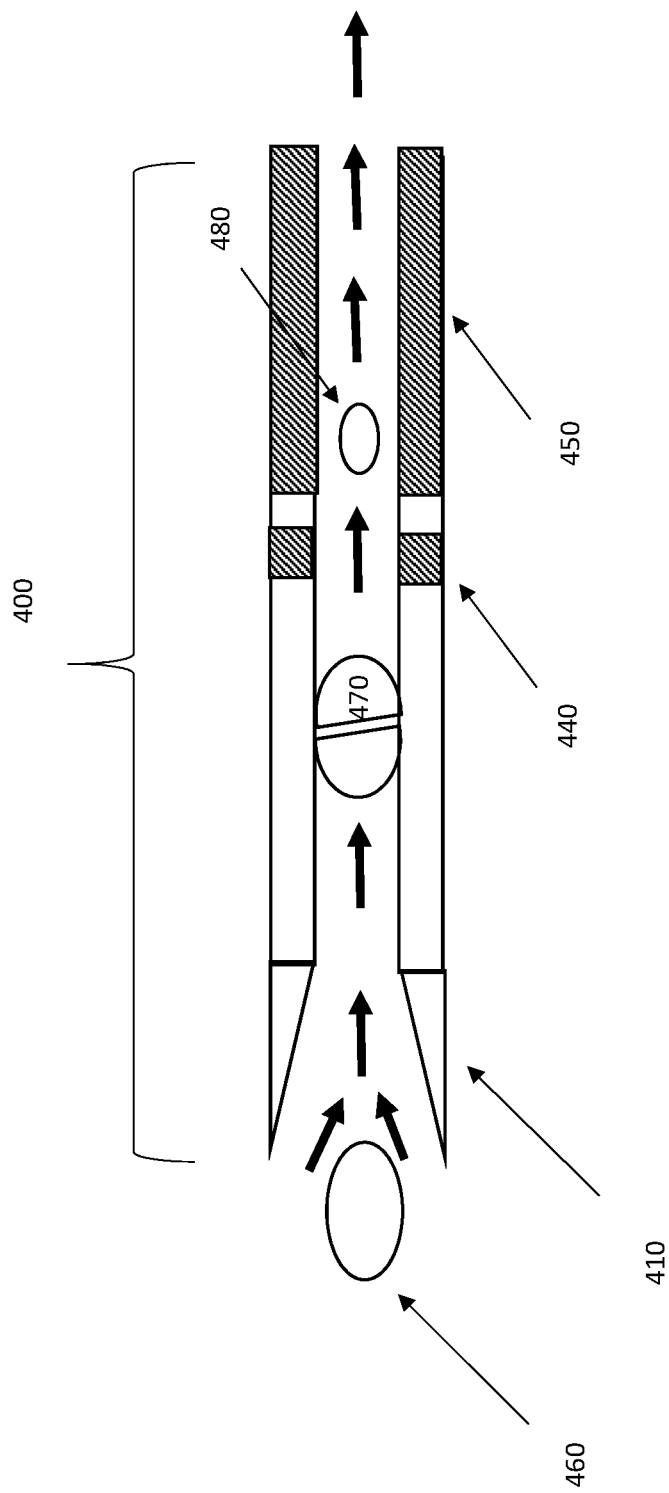
FIG. 4 shows another example of an embodiment of a device provided in accordance with the disclosed embodiments.

FIG. 4 shows another embodiment of the device, called 400 in this figure.

In this example, the walls 410 of the hollow device 400 are tapered so that as the device is rotated (for example by magnetic torques applied on section 440) a suction is created by a current (represented as dark arrows) that pulls pathogen 460 into the fillable section of device 400. Pathogen 470 that has been pulled into the fillable section of the device may be deactivated or destroyed by shear forces or high current or a combination of the two or by heating from magnetic induction the magnetic sections 440 or 450. Components of a healthy body 480 (for example small proteins) may pass through device 400 unharmed. The sequence of operations taken to use the embodiment of the device shown in FIG. 4 are the same or similar to those shown in FIG. 3.

Figure 5:
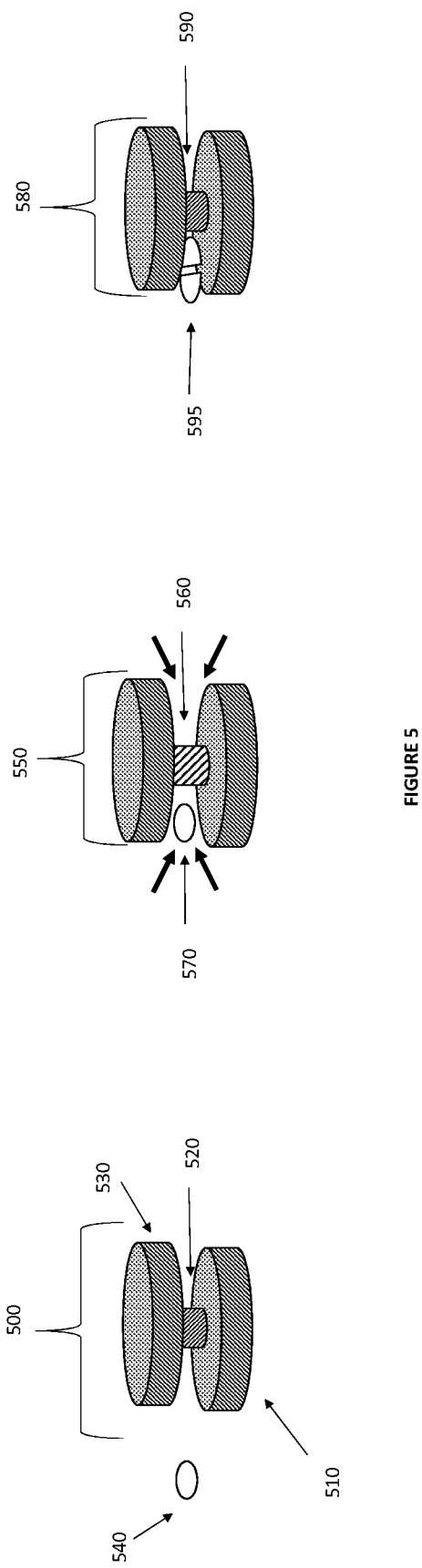
FIG. 5 shows another embodiment of a device provided in accordance with the disclosed embodiments.

FIG. 5 shows another embodiment of the device 500, shown after administration to a body and in the presence of a magnetic field that has been applied by a magnetic actuator located outside the body (not shown in this figure). Device 500 contains anvil sections 530 and 510, both of which contain magnetizable material, and an elastic compressible section 520 (which may be a polymer). The term "anvil" is used to imply the application of force to a structure, as has been applied by scientists who attempt to impose high pressures with diamond anvils (see, for example the PNAS 2018 article by B. Li et al, entitled "Diamond anvil cell behavior up to 4 Mbar"). As a result of the magnetic field that has been applied to the device 500 in the body, sections 530 and 510 are both magnetized and may experience an attractive force to one another, compressing and/or twisting or otherwise deforming section 520. A pathogen 540 is shown nearby (for example within 10 microns). In case 550, the externally applied magnetic field has been reduced or eliminated by the external magnetic actuator, and as a result sections 510 and 530 are no longer attracted to each other and elastic section 520 assumes a different configuration 560. The change in volume of fluid between sections 510 and 530 causes a flow of nearby fluid into the space (fillable section) between those sections 510 and 530, drawing pathogen (now called 570) into that fillable section. In case 580, a magnetic field is once again applied by the external actuator, again compressing or twisting or bending the flexible section (now called 590) and pathogen 595 is crushed or twisted or otherwise damaged by forces or torques applied by sections 510 and 530. The sequence of operations taken to use the embodiment of the device shown in FIG. 5 are the same as shown in FIG. 3.

As discussed above, the apparatus of the disclosed embodiments may include an electromagnetic actuator 230 and at least one device 100, 200, 400, or 500 that is administered to a body 210. Body 210 may be a human, animal, or even an inanimate object like a river. The body contains pathogens 240, 460, 540. The purpose of the disclosed embodiments is to damage, destroy or inactivate the pathogens. Electromagnetic actuator 230 may be used to manipulate device 100, 200, 400, 500 and also to provide images of the body 210 and of the particles 100, 200, 400, 500, as has been taught in U.S. patent application Ser. No. 16/448,915 by I. N. Weinberg, entitled "Method for Acquiring an Image and Manipulating Objects with Magnetic Gradients Produced by One or More Electropermanent Magnet Arrays". Alternatively, imaging may be provided with a different instrument (for example an x-ray CT scanner) while the manipulation, heating and/or rotation of device 100, 200, 400, or 500 is implemented with a different magnetic system.

The walls 110 and 410 and component 520 of the device may be organic (for example plastic), metallic (for example, gold), silica, iron, or other materials. It is understood that manipulation of the device in the body with the external actuator 230, may be used to selectively localize the device (or concentrate a multiplicity of such devices) in a desired location, tissue, part, or otherwise portion of the body (for example the lungs) or to selectively avoid localization of the device in specific parts of the body (for example the heart). It is understood that heating and/or rotating or otherwise actuating the device in the body with the external actuator, as described relating to FIG. 2, may be used to selectively heat or rotate or otherwise actuate the device in a desired portion of the body (for example the lungs) or to selectively avoid excessive or undesirable heating or rotation of the device in the body (for example the heart).

Device 100, 200, 400, 500 may be fabricated according to successive operations using a template, as described in the provisional patent application (No. 63/011,720) by Irving Weinberg entitled "Method and Apparatus of Magnetic Micro-Syringes".

As shown in FIG. 1, binding agent 120 and/or chemoattractant 130 may be bound to the particle via a linker, for example a gold bound thiolate adlayer formed from dithiobis (succinimidyl propionate) as described by J. D. Driskell et al in the Anal. Chem. 2005 journal article entitled "Low-level Detection of Viral Pathogens by a Surface-Enhanced Raman Scattering Based Immunoassay". It is understood that a binding agent and/or chemoattractant may be placed within particles shown in 400 and 500 as well. As shown in FIG. 1, section 140 may be short so that it can be rotated by a helical magnetic field, while section 150 may be relatively long to assist in translation of the particle, as taught by L. O. Mair et al in U.S. Patent application 62/182,901, entitled "Method and Apparatus for Non-Contact Axial Particle Rotation and Decoupled Propulsion". It is understood that similar long and short magnetic sections may be placed within particles shown in 400 and 500 as well to aid in transport. It is understood that not all of particle 100 needs to rotate for device 100 to apply a suction and draw the pathogen into the fillable section of device 100. For example, one section internal or external to particle 100 may rotate and still apply a suction. Alternatively, particle 100 may have a tendril or other attached component, in which the tendril binds to the pathogen and upon rotation or translation of particle 100 draws the pathogen into the particle's fillable section.

It is understood that the particles may be fabricated using template-guided methods, for example as taught by L. O. Mair et al in U.S. patent application 62/292,966, entitled "Roll-to-roll manufacture of inorganic particles using templates and electroplating". It is understood that many of particles 100, 200, 400, or 500 may be administered to a body, for example one billion per dose. It is understood that the particles may be bar-coded (through use of different lengths and thicknesses of magnetic components 440, 450 for example) so that it is possible to keep track of where the particles are in the body. It is understood that devices 100, 200, 400, or 500 may be coated with one or more materials (for example, polyethylene glycol) to make the devices more biocompatible or less harmful to healthy tissues.

It is understood that the use of the disclosed embodiments, as described above in the flow chart shown in FIG. 3, may enable selective use of the disclosed embodiments to eliminate or reduce the toxicity of one type of pathogen as compared to another or to healthy tissue. For example, chemoattractant 130 may attract a particular cell or parasite. Or in another example, the internal dimension of device 400 may be the right size to destroy a 250-nm virus without destroying smaller clotting factors in the blood. Or in another example as shown in FIG. 5, elastic section 520 may be selected so that it is small enough to destroy a 250-nm virus with compression without trapping or destroying smaller or larger structures, and big enough to admit the 250-nm virus but not so big as to admit a blood cell.

It is understood that the profile of the walls 410 of the device 400 need not be a sharp taper as illustrated in FIG. 4 but could be a different profile that would create a suction under rotation of the device. It is understood that the device 100, 200, 400, or 500 may have more than one internal section to trap and damage pathogens.

Operations in the usage of the particle shown in FIG. 4 are similar to the operations shown in FIG. 3. In a first operation 300 (referring again to FIG. 3), one or more particles (for example device 400) are administered to a body (for example orally or by inhalation). In a subsequent operation 310, the particles are optionally guided to a location of interest in the body. Alternatively, the particles may accumulate preferentially in a location of interest, for example if the particles were decorated with an antibody or other means of binding to a specific tissue type or types. Or alternatively the particles could do their work anywhere in the body, or in subsystems such as the circulation of the body.

In a subsequent operation 320 pathogen 460 is attracted by applying a magnetic field to rotate the particle 400 to create a suction that pulls in the pathogen to the interior of device 400.

A subsequent operation 330 is the optional detection of the presence of the pathogen in the interior of the device 400, for example as a result of the pathogen's presence in altering the electromagnetic signal emitted by the particle in response to a changing magnetic field (as has been shown to be detectable with magnetic particle imaging).

In subsequent operation 340 the pathogen may be deactivated, for example by magnetically heating the particle or by rotating the particle to apply destructive shear forces on the pathogen or through the combined action of the current and the forces applied by the walls of the device to the pathogen. The destructive forces may break the capsid or capsule of the pathogen and/or may disrupt the internal contents of the pathogen (for example genetic material such as DNA or RNA). Note that these forces or deactivating operations may not be as effective on small material (for example proteins), thereby increasing the selectivity of the device in deactivating pathogens (as opposed to components that are needed or desirable for health). Alternatively, the particle may incorporate magnetoelectric materials that may apply an electrical pulse to the pathogen.

In subsequent operation 350 the particle may optionally degrade in the body, for example through oxidation of the components or digestion by tissues in the body.

Operations in the usage of the particle shown in FIG. 5 are similar to the operations shown in FIG. 3:

In a first operation 300 (referring again to FIG. 3), one or more particles (for example device 500) are administered to a body (for example orally or by inhalation).

In a subsequent operation 310, the particles are optionally guided to a location of interest in the body. It is understood that some or all of the magnetic components of particle 500 may be fabricated with various magnetic sub-sections that can be used to propel and rotate particle 500 to desired locations deep in the body, for example as taught by A. Nacev et al in the 2015 Nano Letters article entitled "Dynamic inversion enables external magnets to concentrate ferromagnetic rods to a central target". Alternatively, the particles may accumulate preferentially in a location of interest, for example if the particles were decorated with an antibody or other means of binding to a specific tissue type or types. Or alternatively the particles could do their work anywhere in the body, or in subsystems such as the circulation of the body.

In a subsequent operation 320 pathogen 540 is attracted by applying a magnetic field to compress part 520 and then stop applying a magnetic field that releases compression, thereby creating a suction that pulls in the pathogen to the interior of device 550.

A subsequent operation 330 is the optional detection of the presence of the pathogen in the interior of the device 500, for example as a result of the pathogen's presence altering the electromagnetic signal emitted by the particle in response to a changing magnetic field, for example as taught by G. Zabow, S. J. Dodd and A. P. Koretsky in the Nature 2008 letter entitled "Shape-changing magnetic assemblies as high-sensitivity NMR-readable nanoprobes". This property may be useful in assessing viral load in a body, potentially even before the viruses have had a chance to infect cells and cause a measurable response (for example with an antibody serum test).

In subsequent operation 340 the pathogen may be deactivated or otherwise damaged, for example by crushing the pathogen as a result of actuation of the particle by the externally located magnetic actuator. For example the attraction of anvils 530 and 510 to one another could create a force that would crack or otherwise injure the capsid of a virus, thereby exposing the genetic materials within the capsid to native enzymes, or to coatings on 530 or 510 or 520 or to drugs or compounds eluted by these or other particle structures. It is believed that a pressure of about fifty atmospheres can break the capsid, as taught by A. Cordova in the 2003 Biophysical Journal article entitled "Osmotic Shock and the Strength of Viral Capsids". A simple calculation of the magnitude of the force between two magnetic dipoles separated by 250 nm shows that it is many times higher than the force experienced by a small particle by 50 atmospheres of pressure. Alternatively, the pathogen may be deactivated by magnetically heating the particle. It is understood that some or all components of device 100, 200, 400, 500 may be coated with an insulating material to protect other structures in a body from such heat or from electrical effects. Note that these forces or deactivating operations may not be as effective on small structures or components in the body (for example proteins), thereby increasing the selectivity of the device in deactivating pathogens (as opposed to components that are needed or desirable for health). Alternatively, the particle may incorporate magnetoelectric materials that may apply an electrical pulse to the pathogen.

In subsequent operation 350 the particle may optionally degrade in the body, for example through oxidation of the components or digestion by tissues in the body.

It is understood that the strong forces that can be applied by the anvils under the influence of a magnetic field established by the magnetic actuator to inactivate pathogenic materials in the body. For example, the device could be used to nibble away at soft or hard pathogenic structures that are otherwise difficult to remove, for example calcified plaque in an artery or a renal calculus. In such an embodiment, the anvils could be placed at the edge of a magnetic device and transported to specified regions containing pathogenic materials (for example carotid artery, kidney, coronary artery) by the magnetic actuator 230. As described above, because the anvils are close to each other (for example, less than one micron apart), the force created by attraction by the anvils is very strong.

It is understood that the dumbbell structure shown in FIG. 5 is an example of a more generalized structure that increases and decreases its inner volume. One such structure might be a clamshell that opens and closes by applying an external magnetic field to its clam-like components, with stretching and compressing of a supporting post (as in 520).

It is understood that the term magnetic material means a magnetizable material, that is a material that will have a magnetic moment during or after exposure to a magnetic field. It is understood that the illustration of a supporting post (as in 520) is an example of a more generalizable supporting structure, for example a compressible porous material or set of compressible posts that could admit a virus or other pathogen during expansion and transmit damaging force or pressure to the virus or other pathogen during compression. The supporting structure or other elements (e.g. overhanging edges) of the dumbbell structure shown in FIG. 5 could assist in retaining the virus or other pathogen during the compressive phase, for example by trapping the virus or other pathogen.

It is understood that the material composition of 510 and 530 may differ from one another. This property may be useful in applying various forces to the device, for example a repulsive force to open the device after it has clamped down on a pathogen. The repulsive force could be implemented as taught by A. Nacev et al in the 2015 Nano Letters article entitled "Dynamic inversion enables external magnets to concentrate ferromagnetic rods to a central target". The dynamic inversion method can be summarized as applying magnetic pulses that polarize a magnetic material in a desired direction a short time before a second magnetic pulse is applied to create a force. Since the initial polarization takes some time to decay, different materials can be affected differently by the same second magnetic pulse. If anvils 510 and 530 are made of different materials, they can therefore be made to attract or repel each other with appropriate use of the dynamic inversion principle.

It is understood that the genetic materials released after the capsule or capsid or other protective coating of a pathogen has been cracked or otherwise damaged by the device that the genetic materials may be destroyed by compounds naturally present in a body, for example proteases. Alternatively, or additionally, coatings or materials incorporated in (or eluted by) components of device 100, 200, 400, 500 may help to destroy such materials. For example, it is known that iron oxide has antiviral activity, as taught by R. Kumar et al in the 2019 Journal of Infection and Chemotherapy entitled "Iron oxide nanoparticles based antiviral activity of H1N1 influenza A virus".

The device 100, 200, 400, 500 may be cleaned through application of magnetic forces or torques from the external magnetic actuator. For example, rotation and/or translation of the device can be used to remove or displace materials that might clog or otherwise impair transport of pathogens into the device.

It is understood that the term "pathogen drawn in to the internal section of the device" includes the attraction of the pathogen to a chemoattractant, or the binding of the pathogen to a binding site 120 on the wall of the device (in which case the pathogen may have encountered the binding site by diffusion), or the suction of the pathogen into the rotating device or into the volume between cap structures 510 and 530. It is understood that the drawing in of the pathogen may be performed by one or more of the above methods used in combination. It is understood that the term "suction" may be any fluid dynamical force or torque, for example from the creation of a vortex in the fluid as a result of the change in physical configuration of the device. It is understood that the pathogen need not be entirely enclosed within the internal section of the device to be damaged. For example, if only a portion of the pathogen is within the internal section of the device, the pathogen may also be damaged as a result of operation of the disclosed embodiments.

It is understood that components of devices 100, 200, 400, 500 may have actions that are pathogen-specific and which may affect operation. For example, elastic material 520 may have the property that it does not contract when in contact with a normal structure in a body, thereby preventing damage to the structure.

It is understood that the devices 100, 200, 400, 500 described above could destroy many pathogens during the residence of the devices in the body. It is understood that some or all of the devices could potentially be withdrawn from the body under the forces and torques generated by the externally located magnetic actuator.

It is understood that the particles may be administered prophylactically to a person who has been exposed to a pathogen, or who is suspected of having been exposed to a pathogen, in order to reduce the number of viable pathogens in the body and hence reduce the risk of subsequent disease caused by the infection.

The invention claimed is:

1. An apparatus for damaging, or destroying at least one pathogen in a body, the apparatus comprising:
    at least one magnetic actuator external to a body, and
    at least one device containing at least one fillable section and at least one magnetizable material,
    wherein the at least one device is configured to draw a pathogen into the fillable section of the device and damage, or destroy the pathogen within the fillable section of the device,
    wherein the device is configured to destroy or damage the pathogen within the at least one fillable section of the device by shear or other mechanical forces, the forces actuated by magnetic or electromagnetic radiation emitted by the at least one electromagnetic actuator external to the body,
    wherein the at least one device is configured to be delivered into the body orally, by inhalation, or by intravenous injection,
    wherein the device is configured to rotate to draw the pathogen into the fillable section of the device by rotation created suction generated at least in part by actuation of the magnetizable material under the influence of a magnetic field generated by the magnetic actuator to rotate the device.

2. The apparatus of claim 1, wherein the pathogen drawn within the fillable section of the device is damaged or destroyed or damaged by heat generated by the magnetizable material of the device, wherein the heat is generated by electromagnetic radiation emitted by an electromagnetic actuator or antenna external to the body.

3. The apparatus of claim 1, wherein the apparatus is further configured to detect the pathogen by changing a magnetic field generated by the magnetic actuator via imaging.

4. The apparatus of claim 1, wherein a presence or absence of the pathogen in the device is sensed using an electromagnetic actuator or antenna external to the body.

5. The apparatus of claim 1, wherein the device is biodegradable in the body.

6. The apparatus of claim 1, wherein the pathogen is a microbe.

7. The apparatus of claim 1, wherein the pathogen is a cell.

8. The apparatus of claim 1, wherein the device is magnetically bar-coded.

9. The apparatus of claim 1, wherein at least part of the device is at least partly toxic to part of the pathogen.

10. The apparatus of claim 1, wherein at least part of the device is at least partly sensitive to at least part of the pathogen.

11. The apparatus of claim 1, wherein parts of the device are attracted to each other over a sub-micron distance under magnetic field from an actuator external to a body and thereby mechanically inactivate pathogenic materials.

12. A method of destroying or damaging one or more pathogens in a body, the method comprising:
    introducing a device containing magnetizable material and also containing a fillable section into the body and at least one magnetic actuator external to the body;
    drawing the pathogen into the fillable section of the device; and
    damaging, or destroying the pathogen in the fillable section of the device,
    wherein the pathogen within the fillable section of the device is destroyed or damaged by shear or other mechanical forces, the forces actuated by magnetic or electromagnetic radiation emitted by at least one electromagnetic actuator external to the body,
    wherein the at least one device is configured to be introduced orally, by inhalation, or by intravenous injection,
    wherein the device is configured to rotate to draw the pathogen into the fillable section of the device by rotation created suction generated at least in part by actuation of the magnetizable material under the influence of a magnetic field generated by the magnetic actuator to rotate the device.

13. The method of claim 12, wherein the damage or destruction is implemented by rotation of the device.

14. The method of claim 12, further comprising detecting one or more pathogens by magnetic resonance.

15. The method of claim 12, wherein the damage or destruction is implemented by heating of one or more sections of the device.

16. The method of claim 12, wherein the device contains binding sites to increase the effectiveness in damaging or destroying a specific pathogen that binds to those sites.

17. The method of claim 12, wherein dimensions of the device are more effective in damaging or destroying specific-sized pathogens as compared to damaging or destroying objects that are different in size than the pathogen.

18. The method of claim 12, wherein the device is selectively localized in specific portions of the body by the external magnetic actuator.

19. The method of claim 12, where the device is used after a body has been exposed or is suspected to have been exposed to a pathogen in order to prophylactically reduce the likelihood of disease caused at least in part by the pathogen.

* * * * *